US008692024B2

(12) United States Patent (10) Patent No.: US 8,692,024 B2
Kouba et al. (45) Date of Patent: Apr. 8, 2014

(54) METHOD OF PRODUCING N-BUTYRALDEHYDE

(75) Inventors: Jay Kouba, Chicago, IL (US); Mounir Izallalen, Savoy, IL (US); Jill Bradshaw, Champaign, IL (US)

(73) Assignee: Eastman Renewable Materials, LLC, Kingsport, TN (US)

( * ) Notice: Subject to any disclaimer, the term of this patent is extended or adjusted under 35 U.S.C. 154(b) by 73 days.

(21) Appl. No.: 13/368,506

(22) Filed: Feb. 8, 2012

(65) Prior Publication Data

US 2012/0209021 A1  Aug. 16, 2012

Related U.S. Application Data

(60) Provisional application No. 61/442,599, filed on Feb. 14, 2011.

(51) Int. Cl.
*C07C 47/02* (2006.01)
(52) U.S. Cl.
USPC .......................................................... 568/420
(58) Field of Classification Search
USPC .......................................................... 568/420
See application file for complete search history.

(56) References Cited

U.S. PATENT DOCUMENTS

| 6,280,721 | B1 | 8/2001 | Adams et al. |
| 2009/0047718 | A1 | 2/2009 | Blaschek et al. |
| 2009/0305369 | A1 | 12/2009 | Donaldson et al. |
| 2010/0075424 | A1 | 3/2010 | Tracy et al. |
| 2010/0330678 | A1 | 12/2010 | Soucaille |
| 2011/0230682 | A1 | 9/2011 | Schmalisch et al. |
| 2011/0281313 | A1 | 11/2011 | Wach et al. |

FOREIGN PATENT DOCUMENTS

| EP | 2267126 | 12/2010 |
| WO | WO2006130925 | 12/2006 |
| WO | WO2008040387 | 4/2008 |
| WO | WO2008144060 | 11/2008 |
| WO | WO2010069542 | 6/2010 |
| WO | WO2010084349 | 7/2010 |
| WO | WO2012035420 | 3/2012 |

OTHER PUBLICATIONS

Oksana V Berezina et al: "Reconstructing the clostridial n-butanol metabolic pathway in Lactobaci 11 us brevis", Applied Microbiology and Biotechnology, Springer, Berlin, DE, vol. 87, No. 2, Mar. 2, 2010, pp. 635-646, XP819841589, ISSN: 1432-8614 abstract.
Liu S et al: "Functional expression of the thiolase gene thl from *Clostridium beijerinckii* P260 in *Lactococcus lactis* and *Lactobacillus buchneri*", New Biotechnology, Elsevier BV, NL, vo 1 . 27, No. 4, Sep. 30, 2010, pp. 283-288, XP027171907, ISSN: 1871-6784 [retrieved on Jul. 22, 2010] cited in the application abstract.
PCT Intl Search Report for Application PCT/US12/24813 (corresponding to U.S. Appl. No. 13/368,506), Intl fiing date Feb. 13, 2012, mailed Aug. 31, 2012, 8 pages.
Rogers et al: "*Clostridium acetobutylicum* Mutants That Produce Butyraldehyde and Altered Quantities of Solvents.", Applied and Environmental Microbiology, vol. 53, No. 12, Dec. 1, 1987, pp. 2761-2766, XP55021139, ISSN: 0099-2240 the whole document.
Alsaker, et al., "Transcriptional Program of Early Sporulation and Stationary-Phase Events in *Clostridium acetobutylicum*"Journal of Bacteria; Oct. 2005; vol. 187, No. 20; pp. 7103-7118.
Altschul, et al., "Gapped BLAST and PSI-BLAST: a new generation of protein database search programs", Nucleic Acids research, 1997, vol. 25, No. 17, pp. 3389-3402.
Atsumi, et al., "Direct photosynthetic recycling of carbon dioxide to isobutyraldehyde", Nature Biotechnology, Dec. 2009, vol. 27, No. 12, pp. 1177-1182.
Ausubel et al., "Current Protocols in Molecular Biology", John Wiley & Sons, Inc., 2001, Unit 15.0.1-15.8.20.
Clark, et al., "Isolation and Characterization of Mutants of *Clostridium acetobutylicum* ATCC 824 Deficient in Acetoacetyl-Coenzyme A: Acetate/Butyrate:Coenzyme A-Transferase (EC 2.8.3.9) and in Other Solvent Pathway Enzymes", Applied and Environmental Microbiology, Apr. 1989, vol. 55, No. 4, pp. 970-976.
Durre, et al., "Transcriptional Regulation of Solventogenesis in *Clostridium acetobutylicum*", J. Mol. Microbiol. Biotechnology, 2002, vol. 4, No. 3, pp. 295-300.
Guss, et al., "Dcm methylation is detrimental to plasmid transformation in *Clostridium thermocellum*", Biotechnology for Biofuels, Vo.. 5, No. 1, May 1, 2012, pp. 30-30.
Harris, et al., "Northern, Morphological, and Fermentation Analysis of spo0A Inactivation and Overexpression in *Clostridium acetobutylicum* ATCC 824", Journal of Bacteriology, Jul. 2002, vol. 184, No. 13, pp. 3586-3597.
Heap, et al., "ClosTron-targeted mutagenesis", Methods Mol Biol, 2010, vol. 646, 165-82 (Abstract).
Heap, et al., "The ClosTron: A universal gene knock-out system for the genus *Clostridium*", Journal of Microbiological Methods, 2007, vol. 70, pp. 452-464.
Jones, et al., "Actone-Butanol Fermentation Revisited"Microbiological Reviews, Dec. 1986, vol. 50, No. 4, pp. 484-524.
Klapatch, et al., "Restriction endonuclease activity in *Clostridium thermocellum* and *Clostridium thermosaccharolyticum*", Applied Microbiology and Biotechnology, Springer Verlag, Berlin, DE, vol. 45, No. 1-2, Jan. 1, 1996, pp. 127-131.
Lee, et al., "Vector Construction, Transformation, and Gene Amplification in *Clostridium acetobutylicum* ATCC 824a", Annals New York Academy of Science, 1992, vol. 665, pp. 39-51.
Macaluso, et al., "Efficient transformation of *Bacillus thuringiensis* requires nonmethylated plasmid DNA", Journal of Bacteriology, vol. 173, No. 3, Feb. 1, 1991, pp. 1353-1356.
MacNeil, et al., "Characterization of a Unique Methyl-Specific Restriction System in *Streptomyces avermitilis*", Journal of Bacteriology, American Society for Microbiology, Washington, DC, US, vol. 170, No. 12, Dec. 1988, pp. 5607-5612.
Mermelstein, et al., "In Vivo Methylation in *Escherichia coli* by the *Bacillus subtilis* Phage F 3T I Methyltransferase to Protect Plasmids from Restriction upon Transformation of *Clostridium acetobutylicum* ATCC 824", Applied and Environmental Microbiology, Apr. 1993, vol. 59, No. 4, pp. 1077-1081.

(Continued)

*Primary Examiner* — Shawquia Young
(74) *Attorney, Agent, or Firm* — Lee & Hayes, PLLC (57) ABSTRACT

The invention provides method of producing n-butyraldehyde using recombinant solventogenic bacteria and recombinant microorganisms.

22 Claims, 3 Drawing Sheets

(56) References Cited

OTHER PUBLICATIONS

Palmer, et al., "The dam and dcm strains of *Escherichia coli*—a review", Gene, Elsevier, Amsterdam, NL, vol. 143, No. 1, May 27, 1994, pp. 1-12.

The PCT Search Report mailed Sep. 19, 2012 for PCT application No. PCT/US2012/024833, 22 pages.

Petersen, et al., "Molecular Cloning of an Alcohol (Butanol) Dehydrogenase Gene Cluster from *Clostridium acetobutylicum* ATCC 824", Journal of Bacteriology, Mar. 1991, vol. 173, No. 5, pp. 1831-1834.

Ramanu, et al., "Impact of methylation state of plasmid on transformability of *Clostridium beijerinckii* BA101", Abstracts of the General Meeting of the American Society for Microbiology, Washington, US, vol. 106, May 25, 2006, p. 292.

Ramanu, "Optimization of the Electrotransformation efficiency of *Clostridium beijerinickii* BA101", Thesis submitted at the Graduate College of the University of Illinios at Urbana-Champaign, 2006, 96 pages.

Sambrook et al., "Molecular Cloning: A Laboratory Manual", Cold Spring Harbor Laboratory Press, 3rd Edition, 2001, pp. 1.24-1.28.

Scotcher, "Genetic Factors Affecting the Regulation of Solventogenesis in *Clostridium acetobutylicum* ATCC824"Thesis submitted at the Rice University in Houston Texas, Jan. 2005, Abstract, 245 pages.

Scotcher, et al., "SpoIIE Regulates Sporulation but Does Not Directly Affect Solventogenesis in *Clostridium acetobutylicum* ATCC 824", Journal of Bacteriology, Mar. 2005, vol. 187, No. 6, pp. 1930-1936.

Tracy, et al., "Inactivation of sE and sG in *Clostridium acetobutylicum* illuminates their roles in clostridial-cell form biogenesis, granulose synthesis, solventogenesis, and spore morphogenesis", JB Accepts published online ahead of print on Jan. 7, 2011, pp. 1-52.

Tummala, et al., "Antisense RNA Downregulation of Coenzyme A Transferase Combined with Alcohol-Aldehyde Dehydrogenase Overexpression Leads to Predominantly Alcohologenic *Clostridium acetobutylicum* Fermentations", Journal of Bacteriology, Jun. 2003, vol. 185, No. 12, pp. 3644-3653.

Wolfsberg, et al., "Sequence Similarity Searching Using the Blast FAmily of Programs", Current Protocols in Molecular Biology, 1999, Unit 19.3, pp. 19.3.1-19.3.29.

FIG. 1

Control

METHOD OF PRODUCING N-BUTYRALDEHYDE

CROSS REFERENCE TO RELATED APPLICATION

This application claims the benefit of U.S. Provisional Application Ser. No. 61/442,599, filed Feb. 14, 2011, which is incorporated herein by reference in its entirety.

SEQUENCE LISTING

The following application contains sequence listings in computer readable format (CRF), submitted as a text file in ASCII format. The content of the CRF is hereby incorporated by reference.

BACKGROUND

Batch culturing and fermentation processes using microorganisms provide an efficient and cost-effective means of producing biochemicals and bioproducts. Using abundant non-anthropogenic feedstock as the starting material for producing these biomaterials is the goal of many scientists. It is estimated that over one billion dry tons of non-anthropogenic feedstock are available for use each year in the United States, almost half of which is available for under $40 a dry/ton.

As crude oil prices have risen, biochemicals and bioproducts have become increasingly attractive to the chemical and manufacturing world. Biochemicals and bioproducts such as n-butyraldehyde have many characteristics that make them better than most oil-based products, including the following: (a) lower greenhouse gas emissions from its production; (b) lower production costs due to starting materials; (c) fewer renewable starting materials are typically used; and (d) all the same physical properties as petroleum-based n-butyraldehyde. n-Butyraldehyde is used industrial applications in solvents and intermediates. The primary use for n-butyraldehyde, an intermediate formed using the subject technology, is as a chemical intermediate in producing other chemical commodities such as 2-Ethylhexanol (2-EH). 2-EH is widely used in plasticizers, coatings and adhesives. Other products requiring n-butyraldehyde include trimethylolpropane (TMP), n-butyric acid, polyvinyl butyral (PVB), n-butanol, and methyl amyl ketone. Smaller applications include intermediates for producing pharmaceuticals, crop protection agents, pesticides, synthetic resins, antioxidants, vulcanization accelerators, tanning auxiliaries, perfumery synthetics, and flavors.

With successful overproduction of n-butyraldehyde, a shift in use from chemical intermediates to conversion of butanol is predicted. Butanol or butyl alcohol (sometimes also called biobutanol when produced biologically), is a primary alcohol with a 4 carbon structure and the molecular formula of $C_4H_9OH$. Butanol is used as a solvent, as an intermediate in chemical synthesis, and as a fuel. Currently, n-butanol is being considered as an additive to gasoline. The current global market is about 350 million gallons per year with the U.S. market accounting for about 220 million gallons per year. Production of butanol for a gasoline additive could produce a demand of 72 million gallons a day in the United States.

n-Butyraldehyde is traditionally made by the hydroformulation of propylene. Cobalt catalysts were the original catalysts used, but newer rhodium catalysts are now being employed. n-Butyraldehyde can also be produced by the oxidation of butanol or hydrogenation of crotonyl. n-Butyraldehyde has never been successfully produced by an organism on an industrial scale.

Acetone-butanol-ethanol (ABE) fermentation with *Clostridium acetobutylicum* was once a widely used industrial fermentation process providing acetone, which was used to produce cordite. However, production of acetone from propylene has contributed to the downward spiral of ABE fermentation. ABE fermentation for production of butanol has gained interest since the 1980's as a use for gasoline additives, but limitations still prevent industrial scale production. Limitations associated with industrial scale production include: (a) low butanol yield from glucose (15-25%); (b) low reactor productivity (0.5 g/Lh); (c) low final concentrations of less than 15 g/L; and (d) expensive purification. As a result, ABE fermentation is not cost competitive with petroleum-based butanol production. Accordingly, there is a continued need for an inexpensive and effective method of producing both butanol and butanol precursors such as n-butyraldehyde and butyric acid.

n-Butyraldehyde is used as an intermediate in the manufacturing of plasticizers, alcohols, solvents, and polymers, such as 2-ethylhexanol, n-butanol, trimethylolpropane, n-butyric acid, polyvinyl butyral, and methyl amyl ketone. n-Butyraldehyde also is used as an intermediate to make pharmaceuticals, agrochemicals, antioxidants, rubber accelerators, textile auxiliaries, perfumery, and flavors.

n-butyraldehyde conventionally is produced from propylene or butadiene. These two substrates are made from fossil fuels, such as oil and natural gas, which are non-renewable resources for which a limited supply is available. Therefore, there exists a need for new methods of producing n-butyraldehyde.

BRIEF SUMMARY

The current disclosure provides a method of producing n-butyraldehyde comprising (a) providing recombinant solventogenic bacterium with reduced or knocked-out expression of at least one enzyme involved in n-butyraldehyde biodegradation or synthesis of n-butyraldehyde reaction products, i.e., butanol, as compared to a parent bacterium, and (b) culturing the recombinant solventogenic bacterium to produce n-butyraldehyde. In certain embodiments, the current disclosure provides a method of producing n-butyraldehyde comprising (a) providing recombinant solventogenic bacterium with reduced or knocked-out expression of butanol dehydrogenase as compared to a parent bacterium, and (b) culturing the recombinant solventogenic bacterium to produce n-butyraldehyde. "Knocked-out expression" for present purposes can include the deletion of an entire gene of interest, its coding portion, its non-coding portion, or any segment of the gene which serves to inhibit or prevent expression or otherwise render inoperable the gene of interest. A person of ordinary skill in the art of molecular biology would readily understand the term "knocked-out expression" to refer to a recombinant organism having at least one gene rendered inoperable via molecular biology techniques. Moreover, examples of such means to generate recombinant organisms with "knocked-out expression" of specific genes (i.e. recombinant organisms having inoperable genes) are fully described in Sambrook et al., Molecular Cloning: A Laboratory Manual (3$^{rd}$ Ed., 2001); and Ausubel et al. Current Protocols in Molecular Biology (1994).

The current disclosure also provides a method of producing n-butyraldehyde comprising (a) providing a recombinant microorganism that has been prepared from a parent microorganism in which expression of at least one enzyme involved in n-butyraldehyde synthesis has been introduced or amplified, and (b) culturing the recombinant microorganism to produce n-butyraldehyde.

The current disclosure further provides a method of producing n-butyraldehyde comprising: (a) providing a recombinant microorganism that has been prepared from a parent microorganism in which expression of at least one enzyme involved in n-butyraldehyde synthesis has been altered to an extent which increases n-butyraldehyde synthesis during solventogenesis, and (b) culturing the recombinant microorganism under solventogenesis conditions to provide a culture medium containing n-butyraldehyde.

DETAILED DESCRIPTION

The current disclosure provides a method of producing n-butyraldehyde (1-butanal) in a sustainable manner from renewable substrates.

In a first embodiment, the method of producing n-butyraldehyde comprises (a) providing a recombinant solventogenic bacterium with reduced or knocked-out expression of butanol dehydrogenase (which converts n-butyraldehyde to n-butanol) as compared to a parent (e.g., wild-type) bacteria, and (b) culturing the recombinant solventogenic bacterium to produce n-butyraldehyde.

Solventogenic bacteria at least partially produce a solvent, such as n-butanol, ethanol, acetone, or isopropanol. The solventogenic bacteria can be any suitable bacteria, but preferably are solventogenic (e.g., butanologenic) bacteria from Clostridium sp. Particular examples, include, but are not limited to the known n-butanol producing species of Clostrida, C. acetobutylicum, C. beijerinckii (e.g., C. beijerinckii The National Collection of Industrial, Food and Marine Bacteria Accession No. NCIMB 8052 and C. beijerinckii BA101), C. saccharobutylicum, and C. saccharobutylacetonicum. Alternatively, the solventogenic bacteria can be bacteria that previously have been engineered to produce butanol, such as recombinant Lactococcus lactis and Lactobacillus buchneri (see Liu et al., New Biotechnol., 27: 283-288 (2010)).

In an aspect of this embodiment, the recombinant solventogenic bacterium is derived from a Clostridium beijerinckii bacterium containing a butanol dehydrogenase gene comprising a nucleic acid sequence which is at least about 50% identical to a comparative sequence selected from the group consisting of SEQ ID NO. 1, SEQ ID NO. 2, and SEQ ID NO. 3. The recombinant solventogenic bacterium contains at least one of the butanol dehydrogenase gene sequences selected from SEQ ID NO: 1, 2, and 3, wherein the gene sequences include genes comprising a nucleic acid sequence at least about 50% identical to their respective nucleic acid sequences as identified by specific SEQ ID NO as set out below. SEQ ID NO: 1 relates to gi|5292938 (locus Cbei_1722) encoding for NADPH-dependent butanol dehydrogenase. SEQ ID NO: 2 relates to gi|5293392 (locus Cbei_2181) encoding for an NADPH-dependent butanol dehydrogenase. SEQ ID NO: 3 relates to gi|5293624 (locus Cbei_2421) encoding for NADH-dependent butanol dehydrogenase A. For present purposes, these genes include genes comprising a nucleic acid sequence at least about 70%, at least about 80%, at least about 90%, at least about 95%, or even at least about 99% identical to their respective nucleic acid sequences as identified by specific SEQ ID NO.

In another embodiment, the method of producing n-butyraldehyde comprises (a) providing a recombinant microorganism that has been prepared from a parent (e.g., wild-type) microorganism in which expression of at least one enzyme involved in n-butyraldehyde synthesis has been introduced or amplified, and (b) culturing the recombinant microorganism to produce n-butyraldehyde. The enzymes involved in n-butyraldehyde synthesis include thiolase (acetyl-CoA acetyltransferase), 3-hydroxybutyryl-CoA dehydrogenase, crotonase (3-hydroxybutyryl-CoA dehydratase), butyryl-CoA dehydrogenase, phosphotransbutyrylase, butyrylkinase, acetoacetate acetyl-CoA transferase, and butyraldehyde dehydrogenase. Preferably, expression of at least one enzyme (e.g., at least two, at least three, at least four, or five enzymes) selected from the group consisting of thiolase (acetyl-CoA acetyltransferase), 3-hydroxybutyryl-CoA dehydrogenase, crotonase, butyryl-CoA dehydrogenase, butyraldehyde dehydrogenase, and combinations thereof, has been introduced or amplified in the parent microorganism to form the recombinant microorganism.

The microorganism can be bacteria, yeast, or a fungus. In one aspect, the bacteria, yeast, or fungus initially is not solventogenic (produce little or no solvents) or are non-ethanologenic (produce little or no ethanol), non-acetogenic (produce little or no acetate), non-butyrogenic (produce little or no butyrate), and/or non-butanologenic (produce little or no butanol). Preferably, the bacteria, yeast, or fungus initially do not comprise one or more of the genes encoding the enzymes that produce butanol (e.g., n-butanol) and, thus, do not produce butanol.

Examples of suitable microorganisms to be used in the present embodiment include, but are not limited to, Escherichia coli, Pseudomonas butanovora, Streptomyces cinnamonensis, Lactococcus lactis, Lactobacillus buchneri, Thermoanaerobacter ethanolicus, Thermoanaerobacterium thermosaccharolyticum, Thermoanaerobacterium xylanolyticum, Anaeribacteium thermophilum, and non-butanologenic bacteria, such as non-butanologenic Clostridia. Particular species that are known to produce solvents and known to be important platforms for the production of bio-based chemicals and bio-based fuels include, but are not limited to, Clostridium thermocellum, C. phytofermentens, C. carboxidivorans, C. ragsdalei, C. ljungdahlii, C. autoethanogeum, C. celluloyticum, C. cellulovrans, C. papyrosolvens, C. populeti, C. celerescens, C. cellobioparum, C. pasteurianum, C. butyricum, C. tetanomorphum, C. pasteurianum, C. aurantibutyricum, Thermoanaerobacter ethanolicus, Thermoanaerobacterium thermosaccharolyticum, Thermoanaerobacterium xylanolyticum, and Anaerobacterium thermophilum.

The recombinant solventogenic bacterium and/or recombinant microorganism further can have reduced, knocked-out, or no expression of other enzymes involved in the production of solvents. In particular the recombinant solventogenic bacterium and/or recombinant organism can have (a) reduced, knocked-out, or no expression of alcohol dehydrogenase, i.e., alcohol dehydrogenase other than butanol dehydrogenase; (b) reduced, knocked-out, or no expression of lactate dehydrogenase (see, e.g., U.S. 20110230682)); (c) reduced, knocked-out, or no expression of fumarate reductase; (d) reduced, knocked-out, or no expression of a hydrogen-evolving hydrogenase; and/or (e) reduced, knocked-out, or no expression of formate dehydrogenase.

For present purposes, specific genes which are suitable for use, alteration or deletion in the invention can include those whose sequence identity comprises a nucleic acid sequence at least about 50% identical to their respective nucleic acid sequences of interest, say, e.g., at least about 50%, at least about 60%, at least about 70%, at least about 80%, at least about 90%, at least about 95%, at least about 99%, at least about 99.5%, or even at least about 99.9% identical, e.g., at least about 70%.

Non-naturally occurring variants can be made by mutagenesis techniques, including those applied to polynucleotides, cells, or microorganisms. The variants can contain nucleotide substitutions, deletions, inversions and insertions. Variation can occur in either or both the coding and non-coding regions. In certain aspects, non-naturally occurring variants can have been optimized for use in a given microorganism (e.g., Escherichia coli), such as by engineering and screening the enzymes for increased activity, stability, or any other desirable feature. The variations can produce both conservative and non-conservative amino acid substitutions (as compared to the originally encoded product). For nucleotide sequences, conservative variants include those sequences that, because of the degeneracy of the genetic code, encode the amino acid sequence of a reference polypeptide. Variant nucleotide sequences also include synthetically derived nucleotide sequences, such as those generated, for example, by using site-directed mutagenesis but which still encode a biologically active polypeptide.

The term "sequence identity" for example, comprising a "sequence 50% identical to," as used herein, refers to the extent that sequences are identical on a nucleotide-by-nucleotide basis or an amino acid-by-amino acid basis over a window of comparison. Thus, a "percentage of sequence identity" can be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

The terms used to describe sequence relationships between two or more polynucleotides or polypeptides include "comparative sequence," "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides can each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window can comprise additions or deletions (i.e., gaps) of about 20% or less as compared to the reference sequence (which does not comprise additions or deletions) for optimal alignment of the two sequences. Optimal alignment of sequences for aligning a comparison window can be conducted by computerized implementations of algorithms (GAP, BESTFIT, which can be used in association with FASTA, and TFASTA text-based formats in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also can be made to the BLAST family of programs as for example disclosed by Altschul et al., 1997, Nucl. Acids Res. 25:3389. A person of skill in the art of molecular biology would be well aware of the tools and techniques used for gene sequence analyses (e.g. DNA sequence alignments). Moreover, a detailed discussion of sequence analysis can be found in Unit 19.3 of Ausubel et al., "Current Protocols in Molecular Biology," John Wiley & Sons Inc, 1994-1998, Chapter 15.

In one aspect, the parent microorganism is an ethanologenic Clostridia (i.e., Clostridia that produce ethanol). In order for the ethanologenic Clostridia to produce n-butyraldehyde, expression of acetaldehyde dehydrogenase, which converts acetyl-CoA to acetaldehyde, is reduced or knocked-out in the parent microorganism in order to stop the formation of ethanol. Additionally, one or more genes encoding enzymes of the oxidative (to make ATP) and the reductive branches involved in n-butyraldehyde synthesis are introduced into the parent microorganism. Such enzymes include thiolase (which converts acetyl CoA to acetoacetyl-CoA), 3-hydroxybutyryl-CoA dehydrogenase (which converts acetoacetyl-CoA to β-hydroxybutyrl-CoA), crotonase (which converts β-hydroxybutyrl-CoA to crotonyl-CoA), butyryl-CoA dehydrogenase (which converts crotonyl-CoA to butyryl-CoA), phosphotranbutyrylase (which converts butyryl-CoA to butyryl-P), butyrylkinase (butyryl-P to butyrate), acetoacetate acetyl-CoA transferase (which converts butyrate to butyryl-CoA), and butyraldehyde dehydrogenase (which converts butyryl-CoA to butyraldehyde).

Alternatively, one or more genes encoding enzymes of the oxidative and reductive branches involved in n-butyraldehyde synthesis without making butyrate are introduced into the parent microorganism. Such enzymes include thiolase (which converts acetyl-CoA to acetoacetyl-CoA), 3-hydroxybutyryl-CoA dehydrogenase (which converts acetoacetyl-CoA to β-hydroxybutyrl-CoA), crotonase (which converts β-hydroxybutyrl-CoA to crotonyl-CoA), butyryl-CoA dehydrogenase (which converts crotonyl-CoA to butyryl CoA), and butyraldehyde dehydrogenase (which converts butyryl-CoA to butyraldehyde).

In bacteria or microorganisms (e.g., ethanologenic Clostridia) wherein lactate or hydrogen are produced in order to compensate for the reduction-oxidation (redox) imbalance caused by a decrease in the secretion of reduced solvents (e.g., butanol and ethanol), expression of lactate dehydrogenase and/or hydrogen-evolving hydrogenase can be reduced or knocked-out.

In another aspect disclosed herein, the parent microorganism is an acetogenic/butyrogenic Clostridia (i.e., Clostridia that produce acetate, butyrate, or both). This group of Clostridia (e.g., *Clostridium butyricum*) can be modified to reassimilate the acids (i.e., acetate and/or butyrate). In order for the acetogenic/butyrogenic Clostridia to produce n-butyraldehyde, expression of acetoacetate-acetyl-CoA transferase (which converts acetoacetyl-CoA, butyrate, and acetate to acetoacetate, butyryl CoA, and acetyl-CoA, respectively) should be introduced or amplified in the parent microorganism. Additionally, one or more genes encoding enzymes of the oxidative and reductive branches involved in n-butyraldehyde synthesis without making butyrate are introduced. These enzymes include thiolase (which converts acetyl-CoA to acetoacetyl-CoA), 3-hydroxybutyryl-CoA dehydrogenase (which converts acetoacetyl-CoA to β-hydroxybutyrl-CoA), crotonase (which converts β-hydroxybutyrl-CoA to crotonyl-CoA), butyryl-CoA dehydrogenase (which converts crotonyl-CoA to butyryl CoA), and butyraldehyde dehydrogenase (which converts butyryl-CoA to butyraldehyde).

In a further aspect disclosed herein, (a) expression of acetaldehyde dehydrogenase, which converts acetyl-CoA to acetaldehyde, is reduced or knocked-out in a parent microorganism in order to stop the formation of ethanol, (b) one or more genes encoding enzymes of the oxidative and reductive branches involved in n-butyraldehyde synthesis without making butyrate are introduced in the parent microorganism, and (c) expression of lactate dehydrogenase and/or hydrogen-evolving hydrogenase are reduced or knocked-out in the parent microorganism.

The recombinant parent bacteria and microorganisms can be further modified to remove metabolic pathways that could capture reducing equivalents (e.g., NADH and H), such as fumarate reductase (which reduces fumarate to succinate).

The parent bacteria and microorganisms can be modified by any suitable means known in the art. A person of ordinary skill in the art of molecular biology would readily understand the various means to modify the genome of bacteria and microorganism. Moreover, examples of such means to modify bacteria and microorganism genomes are fully described in Sambrook et al., Molecular Cloning: A Laboratory Manual (3rd Ed., 2001); and Ausubel et al. Current Protocols in Molecular Biology (1994).

Alternatively, parent bacteria or microorganisms that are recalcitrant to normal means of genetic manipulation (e.g., due to a potent restriction-modification (RM) system) can be modified by preparing a nucleic acid molecule (e.g., linear DNA or a nucleic acid vector, such as a plasmid or a viral vector) comprising a nucleic acid of interest to be integrated into the parent bacteria or microorganism in a $dcm^-$ bacterium (e.g., *E. coli*). While not wishing to be bound by any particular theory, preparing the nucleic acid molecule in a dcm– bacterium allows the nucleic acid molecule to evade the RM system of the parent bacteria or microorganism into which nucleic acid sequence of interest is to be integrated, as well as increases the chances of homologous recombination occurring between the nucleic acid sequence of interest and the parent bacteria or microorganism with the RM system. Examples of parent bacteria or microorganisms that may be recalcitrant to normal means of genetic manipulation (e.g., due to a potent RM system) include, but are not limited to, *Pelobacter carbinolicus, Pelobacter propionicus, Clostridium difficile, C. botulinum, C. tetani, C. beijerinckii* (e.g., *C. beijerinckii* NCIMB 8052 and the mutant strain BA101), *C. acetobutylicum, C. saccharobutylicum, C. saccharobutylacetonicum, C. thermocellum, C. phytofermentens, C. carboxidivorans, C. ragsdalei, C. ijungdahli, C. autoethanogemum, C. cellulolyticum*, and *C. butyricum.*

In one embodiment, the recombinant solventogenic bacteria or recombinant microorganisms used in the inventive methods constitutively express butyraldehyde dehydrogenase. Constitutive expression of butyraldehyde dehydrogenase can be achieved by any suitable means. For example, the genome of the recombinant bacterium or recombinant microorganism can comprise a nucleic acid sequence encoding butyraldehyde dehydrogenase operably linked to a constitutive promoter. Alternatively, the recombinant bacterium or recombinant microorganism can comprise a plasmid that comprises a nucleic acid sequence encoding butyraldehyde dehydrogenase operably linked to a constitutive promoter.

Following the culturing step of the inventive methods, the culture preferably is enriched for n-butyraldehyde when compared to other fermentation products, such as n-butanol, acetone, ethanol, butyrate, and acetone in order to facilitate the isolation of n-butyraldehyde. In one embodiment, the ratio of n-butyraldehyde:butanol in the resulting culture is at least 0.7:1 (e.g., at least 0.8:1, at least 0.9:1, at least 1:1, at least 1.5:1, at least 2:1, at least 3:1, at least 4:1, at least 5:1, at least 6:1, at least 7:1, at least 8:1, at least 9:1, or at least 10:1).

In another embodiment, the current disclosure provides for a method of producing n-butyraldehyde comprising: (a) providing a recombinant microorganism that has been prepared from a parent microorganism in which expression of at least one enzyme involved in n-butyraldehyde synthesis has been altered to an extent which increases n-butyraldehyde synthesis during solventogenesis, and (b) culturing the recombinant microorganism under solventogenesis conditions to produce a culture medium containing n-butyraldehyde.

The inventive methods further can comprise a step of isolating n-butyraldehyde. Isolation of n-butyraldehyde can be achieved by any suitable means, such as chemical purification, fractionation, solid adsorption (solid phase adsorption), membrane separation, and/or distillation. In particular, the n-butyraldehyde can be isolated using a sweep gas (e.g., gas stripping with carbon dioxide) and/or solvent extraction.

The resulting n-butyraldehyde can be used as the final product or converted to a downstream product, such as 2-ethylhexanol or n-butanol, using known conversion mechanisms. For example, the n-butyraldehyde can be converted to n-butanol using fermentation and/or chemical reduction (e.g., catalytic hydrogenation). Separating the n-butanol from the reaction mixture can be done by any suitable means, such as extraction, distillation, solid adsorption, membrane separation, and/or precipitation.

n-Butyraldehyde, when produced by the method disclosed herein, may be converted into n-butanol. Conversion of n-butyraldehyde into n-butanol may be done by reduction with a borohydride, reducing agent; a metal hydride reducing agent, i.e., lithium aluminum hydride; catalytic hydrogenation; or reduction with an enzyme, i.e., butanol dehydrogenase.

n-Butyraldehyde, when produced by the method disclosed herein, may be converted into 2-ethylhexanol. Conversion of n-butyraldehyde into 2-ethylhexanol is done by an aldol condensation of n-butyraldehyde to produce 2-ethylhexanal, which is then reduced to the alcohol 2-ethylhexanol.

Plasticizers may be prepared from n-butanol by reacting a mono-, di-, or tricarboxylic acid with n-butanol to produce a plasticizing oil. Suitable mono-, di-, or tricarboxylic acid include aliphatic, aromatic and cycloaliphatic acids. Suitable aromatic acids include phthalic, isophthalic, and terephthalic acids.

Plasticizers may be prepared from 2-ethylhexanol by reacting a mono-, di-, or tricarboxylic acid with 2-ethylhexanol to produce a plasticizing oil. Suitable mono-, di-, or trcarboxylic acid include aliphatic, aromatic and cycloaliphatic acids. Suitable aromatic acids include phthalic, isophthalic, and terephthalic acids.

The following examples further illustrate the invention but, of course, should not be construed as in any way limiting its scope.

Example 1

This example describes exemplary experimental conditions for the inventive methods.

Preparation of Plasmids

Before transforming a recipient *Clostridium beijerinckii* BA101, plasmid DNA was prepared from a dcm– derivative of *E. coli* (GM30). The DNA methylation profile of the plasmid DNA was verified by restriction digestion with restriction enzyme pspGI, which does not digest dcm– DNA. The plasmid DNA contained an origin of replication that is functional in *E. coli* and an origin of replication that is functional in *Clostridium* sp. The two plasmids tested were pMTL500E, which is a pAM□1 derivative plasmid, and pGLE, which is a pIM13 derivative plasmid. Both plasmids confer resistance to ampicillin (amp) and erythromycin (erm) that were used for selection in *E. coli* and *C. beijerinckii*, respectively.

Preparation of Electrocompetent Cells

Electrocompetent cells were prepared by germinating spores of *C. beijerinckii* BA101 in TGY broth (tryptone 30 g/L, glucose 20 g/L, yeast extract 10 g/L, and L-cystein 1 g/L) overnight. The cells then were propagated on 100 mL of P2YE (glucose 60 g/L, yeast extract 1 g/L, 1 mL buffer solution ($KH_2PO_4$ 50 g/L, $K_2HPO_4$, and ammonium acetate 200 g/L), 1 mL vitamin stock solution (para-amino-benzoic acid 0.1 g/L, thiamine 0.1 g/L, and biotin 0.001 g/L), and 1 mL of mineral stock solution ($MgSO_4.7H_2O$ 20 g/L, $MnSO_4.H_2O$ 1 g/L, $FeSO_4.7H_2O$ 1 g/L, and NaCl 1 g/L) for 5 hours to reach an absorbance at optical density (OD) 600 nm in the range of 0.8 to 1.0. Cells were washed twice with an equal volume of electroporation buffer (sucrose 0.3 M). Electrocompetent cells were resuspended in 3 mL of the electroporation buffer.

Electroporation

The suspension of electrocompetent cells (400 µL) was mixed with 1 µg of plasmid DNA in an electroporation cuvette (0.4 cm gap) and left on ice for 5 minutes. Electroporation was carried out using a Bio-Rad Gene-Pulser electroporator equipped with a pulse controller with the following electrical settings: voltage of 1.5 kV, resistance of 400□, and capacitance of 25 µF. The cells were transferred to 10 mL of anaerobic TGY medium and then incubated for recovery at 33° C. for 5 hours.

Selection

After recovery, the cell culture was plated on TGY plates containing erm (35 µg/mL). Plates were incubated under an anaerobic atmosphere of 95% $N_2$ and 5% $H_2$. Positive transformants typically form colonies in approximately 36 hours for pMTL500E and 2 days for pGLE plasmids.

Example 2

This example describes that preparation of a recombinant Clostridia in which the expression of butanol dehydrogenase (bdh) is reduced or knocked-out.

To generate a mutagenic fragment of bdh, a portion of the bdh gene from Clostridia is amplified using primers that amplify a portion of the bdh gene. The PCR product is cloned in a vector, such as the pCR 2.1-TOPO vector (Invitrogen, Carlsbad, Calif.), to generate a plasmid (Plasmid 1) comprising the portion of the bdh gene.

The gene providing antibiotic resistance (e.g., erythromycin resistance from pMTL500E) is inserted into the portion of the bdh gene in Plasmid 1.

The resulting plasmid (Plasmid 2) is digested with the appropriate restriction enzymes release the mutagenic fragment composed of the 5' and 3' region of bdh separated by the antibiotic gene. The mutagenic fragment then is ligated into a new plasmid (Plasmid 3), which is subsequently transformed into a dcm– *E. coli* strain as described in Example 1 to produce an unmethylated plasmid (Plasmid 4). Plasmid 4 is electroporated into *Clostridium* following the same procedure and using the same electrical parameters as described in Example 1.

Purified colonies that are resistant to the antibiotic are further confirmed by PCR to provide proof of the presence of the plasmid inside the cell. Positive colonies are cultivated in liquid media in the presence of antibiotic, and when the bacteria reach mid-log phase, the bacteria are spread on TGY plates containing erm (35 µg/mL). After overnight growth, the cells form a bacterial lawn. At this point, plates are replica plated serially onto TGY without antibiotic. These steps are used to remove the selective pressure and enrich for cells that have lost the plasmid.

After 5 transfers, the cells are plated on TGY plates containing erm (35 µg/mL). This step is used to enrich for the cells that still have the resistance gene.

A strain transformed with the same kind of plasmid but without a mutagenic fragment is run in parallel. The absence of any region of identity in this plasmid prevents it from integrating the chromosome of the bacteria. This strain is used as a control to indicate when there is a high probability of the plasmid being lost. There is a greater probability that the plasmid carrying the mutagenic fragment integrated the chromosome, when cultures of the control cannot be recovered from the plates that have antibiotic while colonies from the mutagenized strain could still be isolated.

Confirmation of chromosomal integration is carried out by using pairs of primers where one primer attached to the antibiotic resistance gene and the other to a region outside the region of identity. The generation of PCR product with primer pairs that are specific for 5' or 3' integration is indicative of the presence of mutants that have undergone single 5' or 3' mediated homologous recombination. Double homologous mutants generate a PCR product with both the 3' and the 5' specific primers.

The resulting recombinant Clostridia (both double-homologous recombinant and single integrant recombinant) is used to produce n-butyraldehyde using the inventive methods.

Example 3

Our parent Clostridia, double-homologous recombinant Clostridia and single integrant recombinant Clostridia cells were prepared by germinating spores of each strain in TGY broth (tryptone 30 g/L, glucose 20 g/L, yeast extract 10 g/L, and L-cystein 1 g/L) with (mutant strains) or without (parent strains) 25 ug/mL of erythromycin, for 6 hours. The cells then were propagated on 100 mL of P2YE (glucose 60 g/L, yeast extract 1 g/L, 1 mL buffer solution (KH2PO4 50 g/L, K2HPO4, and ammonium acetate 200 g/L), 1 mL vitamin stock solution (para-amino-benzoic acid 0.1 g/L, thiamine 0.1 g/L, and biotin 0.001 g/L), and 1 mL of mineral stock solution (MgSO4.7H2O 20 g/L, MnSO4.H2O 1 g/L, FeSO4.7H2O 1 g/L, and NaCl 1 g/L) with or without 25 ug/mL erythromycin for 72 hours. Samples were taken after 72 hours and turned in for GC analysis.

Example 4

Figure 1:
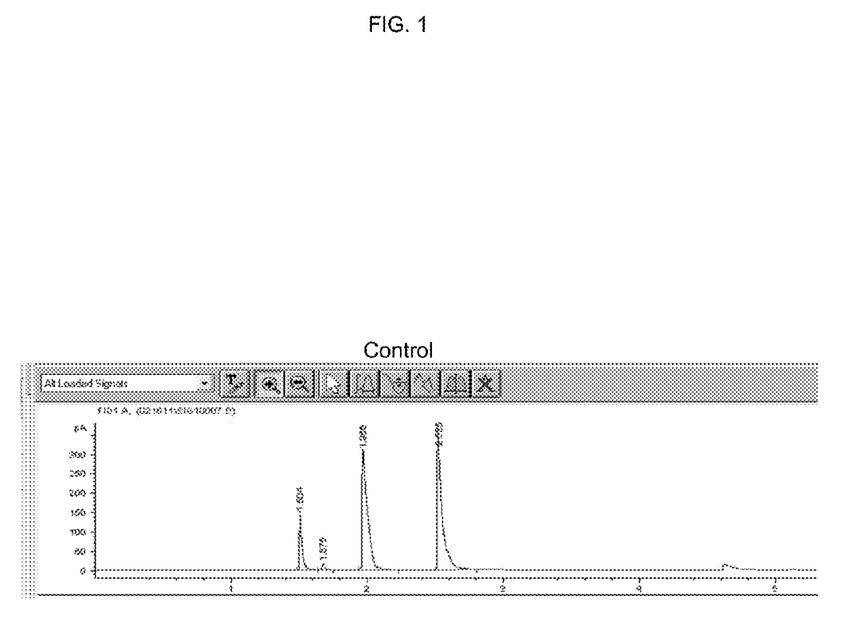
FIG. 1 is a graph depicting gas chromatography analysis of a cultured medium of Clostridium beijerinckii, parent or wild-type strain, showing little if any n-butyraldehyde produced under solventogenic conditions. The graph measures current from a flame ionization detector over time (picoamps/minutes) with n-butyraldehyde eluting at about 1.6 minutes.
Figure 2:
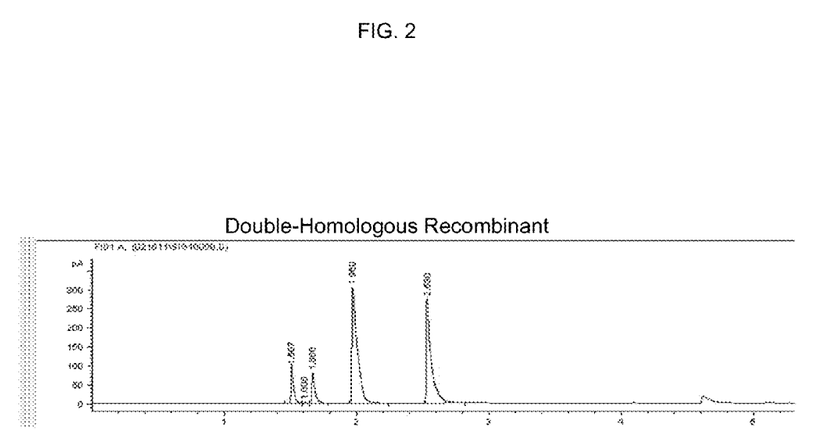
FIG. 2 is a graph depicting gas chromatography analysis of a cultured medium of Clostridium beijerinckii, which is a double homologous recombinant strain of a single knockout of Cbei_2181 showing significant amounts of n-butyraldehyde produced under solventogenic conditions. The graph measures current from a flame ionization detector over time (picoamps/minutes) with n-butyraldehyde eluting at about 1.6 minutes.
Figure 3:
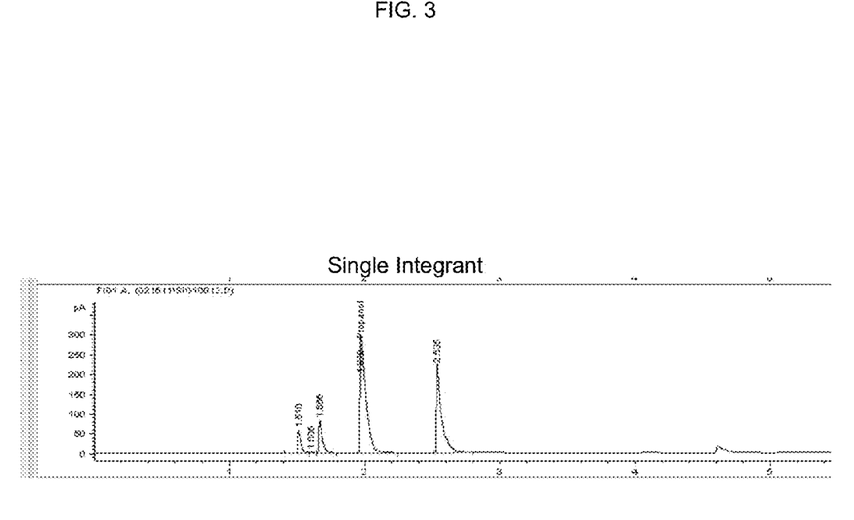
FIG. 3 is a graph depicting gas chromatography analysis of a cultured medium of Clostridium beijerinckii, which is a single integrant recombinant strain of single knockout of a Cbei_2181 showing significant amounts of n-butyraldehyde produced under solventogenic conditions. The graph measures current from a flame ionization detector over time (picoamps/minutes) with n-butyraldehyde eluting at about 1.6 minutes.

Gas chromatographs of three cultured media were obtained for three *Clostridia beijerinckii* bacteria, the first being a parent strain, the second being a double homologous recombinant strain of single knockout of Cbei 2181 gene, and the third being a single integrant strain of Cbei 2181 gene. Respectively, the chromatographs, FIG. 1, FIG. 2, and FIG. 3, measure current over time (picoamps/minutes) with n-butyraldehyde eluting at about 1.6 minutes. A comparison of the three FIGURES shows little if any n-butyraldehyde produced by the parent strain in FIG. 1 at 1.675 minutes, while substantial amounts are produced by both the double-homologous recombinant strain product as shown in FIG. 2 and the single integrant strain product as shown in FIG. 3.

The samples of Example 4 were prepared from cultures grown as described above. Solvents present in the culture supernatant were determined using a Hewlett-Packard/Agilent 6890 gas chromatograph equipped with a flame ionization detector and a J&W Scientific DB-FFAP column (30 mx 0.250 mm capillary). The oven temperature was programmed from 40° C. to 230° C. at etrate of 50° C./min. The injector and detector temperatures were set at 230° C. and 250° C., respectively. Helium was the carrier gas and was set at 30 ml/min All references, including publications, patent applications, and patents, cited herein are hereby incorporated by reference to the same extent as if each reference were individually and specifically indicated to be incorporated by reference and were set forth in its entirety herein.

The use of the terms “a” and “an” and “the” and similar referents set forth herein (especially in the context of the following claims) are to be construed to cover both the singular and the plural, unless otherwise indicated herein or clearly contradicted by context. The terms “comprising,” “having,” “including,” and “containing” are to be construed as open-ended terms (i.e., meaning “including, but not limited to,”) unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., “such as”) provided herein, is intended merely to better illuminate the disclosed subject matter and does not pose a limitation on the scope of the invention unless otherwise claimed. No language in the specification should be construed as indicating any non-claimed element as essential to the practice of the invention.

Multiple embodiments are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of producing n-butyraldehyde comprising:
  (a) providing a recombinant solventogenic bacterium with reduced or knocked-out expression of at least one enzyme involved in either:
    i) n-butyraldehyde biodegradation, or
    ii) synthesis of n-butyraldehyde reaction products, and
  (b) culturing the recombinant solventogenic bacterium to produce n-butyraldehyde.

2. A method of claim 1, wherein said recombinant solventogenic bacterium has reduced or knocked-out expression of butanol dehydrogenase.

3. The method of claim 2, wherein a parent bacterium of the recombinant solventogenic bacterium is from *Clostridium* sp.

4. The method of claim 3, wherein the recombinant solventogenic bacterium is derived from a bacterium selected from the group consisting of *C. acetobutylicum, C. beijerinckii, C. saccharobutylicum,* and *C. saccharobutylacetonicum*.

5. The method of claim 4, wherein the recombinant solventogenic bacterium is derived from a *C. beijerinckii* bacterium which contains at least one butanol dehydrogenase gene; comprising a nucleic acid sequence which is at least about 70% identical SEQ ID NO: 1, SEQ ID NO. 2, or SEQ ID NO. 3.

6. The method of claim 5, wherein the butanol dehydrogenase gene comprises a nucleic acid sequence at least about 80% identical to SEQ ID NO:. 1, SEQ ID NO. 2, or SEQ ID NO. 3.

7. The method of claim 5, wherein the butanol dehydrogenase gene comprises a nucleic acid sequence which is at least about 90% identical to SEQ ID NO said comparative sequence selected from the group consisting of SEQ ID NO. 1, SEQ ID NO. 2, or SEQ ID NO. 3.

8. The method of claim 5, wherein the recombinant solventogenic bacterium is derived from a *C. beijerinckii* bacterium which contains the butanol dehydrogenase gene containing SEQ ID NO: 1.

9. The method of claim 5, wherein the recombinant solventogenic bacterium is derived from a *C. beijerinckii* bacterium which contains the butanol dehydrogenase gene containing SEQ ID NO: 2.

10. The method of claim 5, wherein the recombinant solventogenic bacterium is derived from a *C. beijerinckii* bacterium which contains the butanol dehydrogenase gene containing SEQ ID NO: 3.

11. The method of claim 5 wherein at least one of SEQ ID NO: 1, SEQ ID NO: 2 and SEQ ID NO: 3 is reduced or knocked out in the recombinant solventogenic bacterium.

12. The method of claim 5 wherein the SEQ ID NO: 2 is knocked out in the recombinant solventogenic bacterium.

13. The method of claim 4, wherein the recombinant solventogenic bacterium is derived from a *C. beijerinckii* which is NCIMB 8052 or BA 101.

14. The method of claim 2, wherein the bacterium is selected from recombinant *Lactococcus lactis* and recombinant *Lactobacillus buchneri*.

15. The method of claim 2, wherein the recombinant solventogenic bacterium constitutively expresses butyraldehyde dehydrogenase.

16. The method of claim 2, wherein the recombinant solventogenic bacterium comprises a nucleic acid sequence encoding butyraldehyde dehydrogenase operably linked to a constitutive promoter.

17. The method of claim 2, wherein the recombinant solventogenic bacterium has reduced or knocked-out expression of alcohol dehydrogenase as compared to a parent bacterium.

18. The method claim 2, wherein the recombinant solventogenic bacterium has reduced or knocked-out expression of lactate dehydrogenase as compared to a parent bacterium.

19. The method of claim 2, wherein the recombinant solventogenic bacterium has reduced or knocked-out expression of a hydrogen-evolving hydrogenase as compared to a parent bacterium.

20. The method of claim 2, wherein the recombinant solventogenic bacterium has reduced or knocked-out expression of formate dehydrogenase as compared to a parent bacterium.

21. The method of claim 2, further comprising isolating n-butyraldehyde.

22. The method of claim 21, wherein the n-butyraldehyde is isolated by a method selected from the group consisting of using a sweep gas, gas stripping with carbon dioxide, distillation, solvent extraction, solid adsorption, and membrane separation.

* * * * *

SEQUENCE LISTING

```
<160> NUMBER OF SEQ ID NOS: 3

<210> SEQ ID NO 1
<211> LENGTH: 1167
<212> TYPE: DNA
<213> ORGANISM: Clostridium beijerinckii

<400> SEQUENCE: 1
atggcacgtt ttactttacc tagggacttg tatcatggag aaggggcact tgaagtactt      60
aaaactttaa aaggcaaaaa agcttttgta gttgttggtg gaggatcaat gaaaagattt     120
ggttttctta aacaagttga agattattta acagaagcag gaatggaagt agaactattt     180
gaaggagtag aaccagatcc atcagtagaa acagtaatga agggtgccga agcaatgaga     240
aacttcgagc ctgattggat agttgctatg ggtggaggat caccaataga tgctgcaaaa     300
gctatgtgga tattctatga atacccagat tttacttttg aacaagctgt tgttccattt     360
ggtttaccag agcttagaca aaaagctaaa tttgtagcta ttccatcaac aagtggtaca     420
gctacagaag ttacagcttt ttcagttata acaaattaca cagaaaagat taaatatcct     480
ttagctgatt ttaacataac tccagatata gcaatagttg atccagtatt agctcaaact     540
```

-continued

| | |
|---|---|
| atgccaaaaa cattaacagc tcatactgga atggatgcac taactcatgc tatagaagca | 600 |
| tatactgcat cgcttagatc aaattttct gatcctttag caattaaggc attgcaaatg | 660 |
| gtacaagaaa atttaatcaa gtcttttgaa ggagacaagg aagctagaaa tctaatgcat | 720 |
| gaagctcaat gtttagcagg aatggcattt tctaatgcat tacttggaat agttcattca | 780 |
| atggctcaca aggttggtgc tgtattccat attcctcatg gatgtgcgaa tgctatattc | 840 |
| ttaccatatg taattcaata aatagaaca aaatgcgaag atagatatgc tgatattgct | 900 |
| agagcattaa aattagaagg aaacacagat tcagaattaa ctgattcatt aattggaatg | 960 |
| attaataaaa tgaatagtga tttaaatatt cctcattcaa tgaaagaata tggagttact | 1020 |
| gaagaagatt ttaaagcaaa tctttcattc attgctcata atgcagtgtt agatgcatgt | 1080 |
| acaggatcaa atcctagaga aatagatgat gcgacaatgg aaaaactatt tgaatgcaca | 1140 |
| tattatggga caaaggttga actatag | 1167 |

<210> SEQ ID NO 2
<211> LENGTH: 1167
<212> TYPE: DNA
<213> ORGANISM: Clostridium beijerinckii

<400> SEQUENCE: 2

| | |
|---|---|
| atggcacgtt ttactttacc aagagacatt tatcatggag aaggagcact tgaggcactt | 60 |
| aaaactttaa aaggtaagaa agctttctta gtagttggtg gcggatcaat gaaaagattt | 120 |
| ggatttctta acaagttgga agattattta aagaagcag gaatggaagt agaattattt | 180 |
| gaaggtgttg aaccagatcc atcagtggaa acagtaatga aaggcgcaga agctatgaga | 240 |
| aactttgagc ctgattggat agttgcaatg ggtggaggat caccaattga tgctgcaaag | 300 |
| gctatgtgga tattctacga ataccagat tttacttttg aacaagcagt tgttccattt | 360 |
| ggattaccag accttagaca aaaagctaag tttgtagcta ttccatcaac aagcggtaca | 420 |
| gctacagaag ttacagcatt ctcagttatc acaaattatt cagaaaaaat taatatcct | 480 |
| ttagctgatt taacataac tccagatata gcaatagttg atccagcact tgctcaaact | 540 |
| atgccaaaaa ctttaacagc tcatactgga atggatgcat taactcacgc tatagaagca | 600 |
| tacactgcat cacttcaatc aaatttctca gatccattag caattaaagc tgtagaaatg | 660 |
| gttcaagaaa atttaatcaa atcatttgaa ggagataaag aagctagaaa tctaatgcat | 720 |
| gaagctcaat gtttagctgg aatggcattt tctaatgcat tacttggaat agttcactca | 780 |
| atggctcata aggttggtgc tgtattccat attcctcatg gatgtgcaaa tgctatattt | 840 |
| ttaccatatg taattgagta taacagaaca aaatgcgaaa atagatatgg agatattgcg | 900 |
| agagccttaa aattaaaagg aaacaatgat gccgagttaa ctgattcatt aattgaatta | 960 |
| attaatggat taaatgataa gttagagatt cctcactcaa tgaaagagta tggagttact | 1020 |
| gaagaagatt ttaaagctaa tctttcattt atcgctcata acgcagtatt agatgcatgc | 1080 |
| acaggatcaa atcctagaga aatagatgat gctacaatgg aaaaattatt tgaatgcaca | 1140 |
| tactatggaa ctaaagttaa tttgtaa | 1167 |

<210> SEQ ID NO 3
<211> LENGTH: 1164
<212> TYPE: DNA
<213> ORGANISM: Clostridium beijerinckii

<400> SEQUENCE: 3

| | |
|---|---|
| atggaaaatt taattattc aatacctact aaagtttatt ttggaaaagg gcaaatcaaa | 60 |

```
aatcttgctg ccataattaa agaatctggt aataaaatac ttatagcata tggcggagga      120
agtattaaga aaatggggtt atacgatgaa atgattaaaa tattaaatga taattcaata      180
tcatatgttg aattgtcagg aatagaacca aatccaagaa ttgaaacagt aagaaaagga     240
attaaaattt gtaaggaaaa taatgttgaa gtagttcttg ctgtaggagg cggaagtaca    300
atagattgtg cgaaagttat tgcggcagga gtaaaatacg aaggagatcc atgggattta    360
gtaactagtc cacaaaaaat taatgaagta ttgcctatag taacaatatt aacactatca    420
gcgactggtt ctgagatgga tccacatgct gtgatttctg atatgacaac taatcaaaaa   480
ttgggtacag gtcatgaaaa tatgaaacca aaagcttcaa ttttagatcc tgaatatact   540
tattcagttc ctaaaaatca aactgcagct ggaactgctg atattatgag tcatatattt   600
gaaacttatt ttaatcatac aaagggtgtg gatatccaag atagtacagc cgaaggatta  660
cttagagctt gcataaaata tggtaagatt gcaatagaga atccaaagga ttacgatgca   720
agagcaaatt taatgtgggc ttcaagctgg gctattaatg gcttgatttc atatggaaca   780
aattcacctt gggtggtaca tccaatggag catgaattga gtgcttttta tgatataaca    840 catgggggttg gattggctat attaacacct cattggatga aatattcttt agacgatact   900
actgttttta agtttgctca atatggaata aatgtttggg gaatagataa aaacttagat  960
aagtttgaaa tagcaaataa agcaatagaa aagacatctg aattcttttaa ggaattgggt  1020 ataccaagta ctttaaggga agttggcatt gaagaagata agttagaatt aatggcaaaa  1080
aaggctatga atccatattt taagtatgct tttaagccat tagatgaaaa tgatatatta  1140 aagatttttta aagcagcact ttag                                           1164
```